United States Patent [19]
Merkus

[11] Patent Number: 5,955,454
[45] Date of Patent: Sep. 21, 1999

[54] NASAL PHARMACEUTICAL COMPOSITION CONTAINING A PROGESTOGEN

[75] Inventor: Franciscus Merkus, Kasterlee, Belgium

[73] Assignee: Adir et Compagnie, Courbevoie, France

[21] Appl. No.: 08/522,254

[22] PCT Filed: Mar. 24, 1994

[86] PCT No.: PCT/FR94/00321

§ 371 Date: Sep. 11, 1995

§ 102(e) Date: Sep. 11, 1995

[87] PCT Pub. No.: WO94/22450

PCT Pub. Date: Oct. 13, 1994

[30] Foreign Application Priority Data

Mar. 26, 1993 [BE] Belgium .................................. 9300296

[51] Int. Cl.$^6$ ...................................................... A61K 31/56

[52] U.S. Cl. ............................ 514/177; 514/178; 514/182

[58] Field of Search ...................................... 514/177, 178, 514/182

[56] References Cited

FOREIGN PATENT DOCUMENTS 0 349 091  1/1990  European Pat. Off. .
0 463 653  1/1992  European Pat. Off. .

*Primary Examiner*—Kimberly Jordan
*Attorney, Agent, or Firm*—The Firm of Gordon W. Hueschen

[57] ABSTRACT

The invention relates to a nasal pharmaceutical preparation suitable for nasal administration containing a progestogen and a methylated β-cyclodextrin having a degree of substitution of between 0.5 and 3.0 and hard gelatin capsules containing the same.

8 Claims, 1 Drawing Sheet

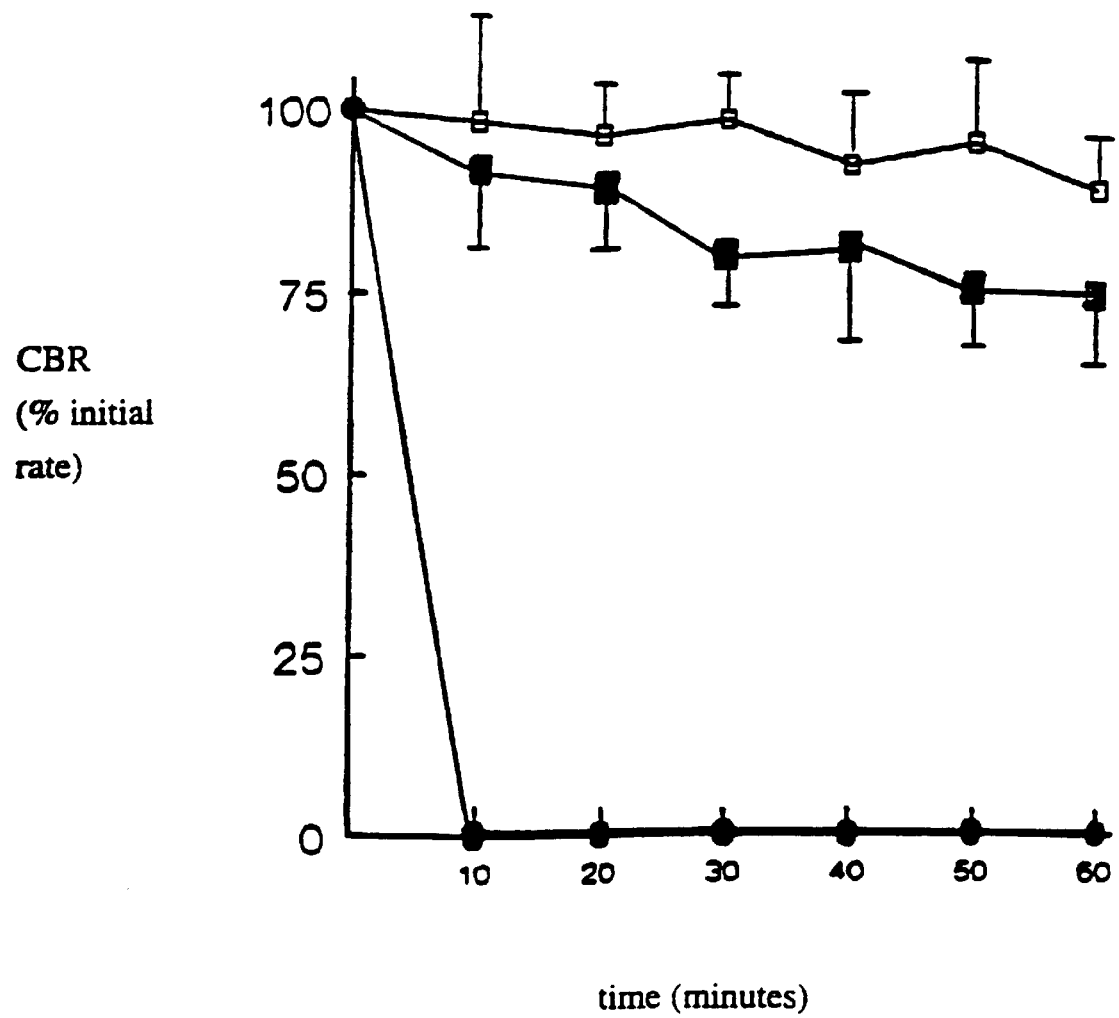

NASAL PHARMACEUTICAL COMPOSITION CONTAINING A PROGESTOGEN

This application is a 371 of PCT/FR94/00321, filed Mar. 24, 1994.

TECHNICAL FIELD

The invention relates to a nasal pharmaceutical preparation having a composition and a form suitable for nasal administration, such as nasal drops and nasal spray, suspensions, gels, ointments, creams and powders, containing a progestogen, for example norethisterone (acetate).

PRIOR ART

Progestogens are used in the treatment of menstrual disorders, alone or in combination with estrogens. Progestogens are also used in the case of endometriosis and of certain cancers. In hormone replacement therapy in (post) menopausal women, progestogens are added to estrogen treatment in order to prevent carcinoma of the endometrium. Similarly, as a contraceptive, progestogens are used, alone or in combination preparations, in oral treatment or as injectable retard preparations. Important examples of progestogens are progesterone, which is a natural hormone, and synthetic progestogens such as norethisterone (acetate), levonorgestrel, norgestrel, desogestrel, gestodene, lynestrenol, ethynodiol diacetate, norgestimate, 3β-hydroxydesogestrel, 19-norprogesterone, medroxyprogesterone (acetate), dydrogesterone, (no)megestrol (acetate), cyproterone (acetate) or medrogestone.

Norethisterone (17α-ethinyl-17β-hydroxyestr-4-en-3-one, norethindrone, NET) is a synthetic progestogen which is used in many countries in steroid preparations used in oral contraceptives, and also as a progestogen administered alone. In addition, norethisterone acetate (NETA) is used in some formulations. After absorption, it is hydrolyzed to norethisterone.

After oral administration, blood NET levels are obtained which are only approximately 60% of those obtained after intravenous administration (D. J. Black et al., Clin. Pharm. Therap. 1978; 24:439–447). This demonstrates that NET is metabolized in the intestinal wall and the liver after absorption via the oral route ("first-pass" effect). As a result, the oral administration of NET is not very effective and leads to a needless loading of the body with drug. With the aim of decreasing this effect, an NET nasal spray has recently been developed and studied in 8 volunteers (T. C. Anand Kumar et al., Contraception 1991; 44:245–267). The authors show that the application of NET via the nasal route in women is of great interest for use in contraceptive preparations. In previous publications, good results have also been described with the same nasal NET formulation in monkeys (V. Puri et al., J. Reprod. Fert. 1986; 76:215–220) and women (R. S. Shah et al., Contraception 1985; 32:135–147). The nasal formulation employed in these studies was prepared as follows. The norethisterone was dissolved in a propylene glycol/ethanol/water (3:3:4 by volume) solution. The dose of NET administered via the nasal route in the study published in 1991 was 300 μg of NET daily in each woman. The nebulizer used delivered 150 μg of NET in each nasal spraying of 100 μl. The requisite dose of 300 μg of NET was delivered by spraying 100 μl once daily in each nostril.

The medicinal products and the additives employed in nasal formulations of medicinal products should not be detrimental to the nasal epithelium and nasal mucociliary clearance. The influence of medicinal products and of additives on the functioning of the cilia in the nose is a crucial parameter (W. A. J. J. Hermens and F. W. H. M. Merkus, Pharm. Res. 1987; 4:445–449, and F. W. H. M. Merkus et al., J. Controlled Release 1993; 24:201–208).

In experiments conducted by the Applicant, the nasal NET formulation dissolved in a propylene glycol/ethanol/water (3:3:4 by volume) mixture was seen to be very toxic with respect to the ciliary movement of ciliary tissue (as shown in the attached FIGURE). The ciliary movement of human nasal tissue is stopped rapidly in a few minutes by this formulation. Nasal mucociliary clearance, in which the ciliary movement is the most important parameter, must not be disturbed by medicinal product formulations, since it constitutes the most important defence mechanism for protecting the respiratory tract against serious infections.

DESCRIPTION OF THE INVENTION

The invention relates to a new formulation intended for the application of a progestogen via the nasal route. This formulation must display good bioavailability (rate and extent of absorption) and, equally important, must not display any toxicity towards the nasal epithelial membranes and ciliary movement.

To this end, the nasal formulation according to this invention contains a cyclodextrin, especially a β-cyclodextrin, and more especially a methylated β-cyclodextrin having a degree of substitution of between 0.5 and 3.0.

The nasal progestogen composition according to this invention does not display ciliotoxicity. Experiments to study the effect of the new formulation on ciliary beat rate reveals virtually no effect after 1 hour of contact, whereas the formulation containing ethanol and propylene glycol was extremely ciliotoxic in a few minutes (as shown in the attached FIGURE). The formulation according to this invention contains no organic solvent, and consists of a progestogen, for example norethisterone, with one or more cyclodextrins, especially a methylated β-cyclodextrin having a degree of substitution of between 0.5 and 3.0 and/or β-cyclodextrin.

After administration of this new nasal formulation containing NETA, the Applicant found blood NET levels comparable with the levels obtained after parenteral administration, testifying to an excellent bioavailability after nasal administration.

EXAMPLE 1

| | |
|---|---|
| Norethisterone (acetate) | 150 mg |
| Methylated β-cyclodextrin | 1.5 grams |
| Benzalkonium chloride | 0.01% |
| EDTA-Na | 0.05% |
| NaCl | 0.9% |
| Distilled water q.s. | 100 ml |

1 spraying = 100 μl = 150 μg of norethisterone (acetate)

EXAMPLE 2

| | |
|---|---|
| Norethisterone (acetate) | 100 mg |
| β-Cyclodextrin | 1.5 grams |
| Benzalkonium chloride | 0.01% |
| EDTA-Na | 0.05% |
| NaCl | 0.9% |
| Hydroxypropylmethylcellulose | 0.1–2% |
| Distilled water q.s. | 100 ml |

100 μl of gel = 100 μg of norethisterone (acetate)

EXAMPLE 3

| | |
|---|---|
| Norethisterone (acetate) | 200 mg |
| Methylated β-cyclodextrin D.S. 1.8 | 2 grams |
| Benzalkonium chloride | 0.01% |
| EDTA-Na | 0.1% |
| NaCl | 0.9% |
| Distilled water q.s. | 100 ml |

1 spraying = 100 μl = 200 μg of norethisterone (acetate)

The examples of NET(A) nasal formulations described here are given by way of illustration of the invention, no limitation being implied thereby. In addition, other progestogens may be included in these nasal formulations, such as levonorgestrel, norgestrel, desogestrel, gestodene, lynestrenol, ethynodiol diacetate, norgestimate, 3β-hydroxydesogestrel, 19-norprogesterone, medroxyprogesterone (acetate), dydrogesterone, (no)megestrol (acetate) or medrogestone.

In addition, the inclusion in nasal formulations of cyclodextrins other than those mentioned could be envisaged.

Furthermore, additives other than those mentioned in the examples, and which are known in the pharmaceutical literature, may be employed in the formulation, such as preservatives, viscosity agents, agents influencing osmolarity, complexing agents (such as, for example, sodium edetate), surfactants and agents which influence the pH and tonicity of the nasal formulation. The nasal preparation may be administered in nasal drops, nasal spray, gel, ointment, cream, powder or suspension, using a dispenser or a device (for example a single-dose ampoule, an atomizer, a nebulizer, a pump, a nasal pad, a nasal sponge or a hard gelatin capsule) or any other method of nasal administration which is known in the pharmaceutical literature.

BRIEF REFERENCE TO THE DRAWING

The attached FIGURE shows the reduction in ciliary beat rate (CBR) of human adenoid tissue under the influence of two different norethisterone formulations (n=6). The formulation containing norethisterone in propylene glycol/ethanol/water (3:3:4 by volume) causes an immediate and total ciliostasis in a few minutes (represented in the FIGURE by —●—).

The influence of the norethisterone formulation shown in Example 1 is minimal on CBR, even after 60 minutes of contact (represented in the FIGURE by —■—).

By way of reference (blank), the CBR under the influence of a pure Locke-Ringer solution is shown in the FIGURE (—□—).

I claim:

1. A nasal pharmaceutical composition suitable for nasal administration, containing norethisterone, norethisterone acetate, levonorgestrel, norgestrel, desogestrel, gestodene, lynestrenol, ethynodiol diacetate, norgestimate, 3β-hydroxydesogestrel, 19-norprogesterone, dydrogesterone, nomegestrol acetate, cyproterone acetate, or medrogestone, and a methylated β-cyclodextrin having a degree of substitution of between 0.5 and 3.0.

2. The nasal pharmaceutical composition as claimed in claim 1, which also contains a preservative and/or a viscosity agent and/or an agent influencing osmolarity and/or a complexing agent and/or an agent influencing the pH of the composition.

3. A hard gelatin capsule intended for nasal administration, containing a nasal pharmaceutical composition as claimed in claim 1.

4. The nasal pharmaceutical composition as claimed in claim 1, which contains norethisterone acetate, desogestrel, nomegestrel acetate, levonorgestrel, or dydrogesterone.

5. The nasal pharmaceutical composition as claimed in claim 4, which also contains a preservative and/or a viscosity agent and/or an agent influencing osmolarity and/or a complexing agent and/or an agent influencing the pH of the composition.

6. A hard gelatin capsule intended for nasal administration, containing a nasal pharmaceutical composition as claimed in claim 4.

7. The nasal pharmaceutical composition as claimed in claim 4, which also contains sodium edetate as a complexing agent.

8. The nasal pharmaceutical composition as claimed in claim 1, which also contains sodium edetate as a complexing agent.

* * * * *